(12) United States Patent
Garnier et al.

(10) Patent No.: US 7,670,459 B2
(45) Date of Patent: Mar. 2, 2010

(54) SOFT AND DURABLE TISSUE PRODUCTS CONTAINING A SOFTENING AGENT

(75) Inventors: Gil Bernard Didier Garnier, Neenah, WI (US); Michael Ralph Lostocco, Appleton, WI (US); Troy Michael Runge, Neenah, WI (US); Thomas Hampshire Schulz, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 804 days.

(21) Appl. No.: 11/026,252

(22) Filed: Dec. 29, 2004

(65) Prior Publication Data

US 2006/0137842 A1 Jun. 29, 2006

(51) Int. Cl.
- *D21H 17/34* (2006.01)
- *D21H 17/59* (2006.01)
- *D21H 21/10* (2006.01)

(52) U.S. Cl. .............. 162/164.4; 162/158; 162/164.1; 162/164.3; 162/166; 162/168.2; 162/168.3

(58) Field of Classification Search .......... 162/158, 162/164.1, 164.3, 164.4, 166, 168.2, 168.3
See application file for complete search history.

(56) References Cited

U.S. PATENT DOCUMENTS

| | | |
|---|---|---|
| 1,812,832 A | 6/1931 | Rafton |
| 3,056,714 A | 10/1962 | Feigley, Jr. et al. |
| 3,128,311 A | 4/1964 | Shirley et al. |
| 3,152,998 A | 10/1964 | Moss |
| 3,155,728 A | 11/1964 | Lesene |
| 3,236,895 A | 2/1966 | Lee et al. |
| 3,322,725 A | 5/1967 | Hunter et al. |
| 3,347,926 A | 10/1967 | Zech |
| 3,436,359 A | 4/1969 | Hubin et al. |
| 3,556,932 A | 1/1971 | Coscia et al. |
| 3,556,933 A | 1/1971 | Willaims et al. |
| 3,654,370 A | 4/1972 | Yeakey |
| 3,671,502 A | 6/1972 | Samour et al. |
| 3,677,886 A | 7/1972 | Forssblad et al. |
| 3,700,623 A | 10/1972 | Keim |
| 3,770,575 A | 11/1973 | Ball |
| 3,772,076 A | 11/1973 | Keim |
| 3,779,912 A | 12/1973 | Redmore et al. |
| 3,855,158 A | 12/1974 | Petrovich et al. |
| 3,899,388 A | 8/1975 | Petrovich et al. |
| 3,994,771 A | 11/1976 | Morgan, Jr. et al. |
| 4,013,514 A | 3/1977 | Wildi et al. |
| 4,014,736 A | 3/1977 | Sexton |
| 4,014,933 A | 3/1977 | Boettger et al. |
| 4,049,493 A | 9/1977 | Lare |
| 4,081,319 A | 3/1978 | Conway |
| 4,093,506 A | 6/1978 | Richter |
| 4,093,812 A | 6/1978 | Rainer |
| 4,129,528 A | 12/1978 | Petrovich et al. |
| 4,129,722 A | 12/1978 | Iovine et al. |
| 4,144,122 A | 3/1979 | Emanuelsson et al. |
| 4,147,586 A | 4/1979 | Petrovich et al. |
| 4,153,581 A | 5/1979 | Habermann |
| 4,210,489 A | 7/1980 | Markofsky |
| 4,222,921 A | 9/1980 | Van Eenam |
| 4,251,410 A | 2/1981 | Danner et al. |
| 4,310,384 A | 1/1982 | Meredith et al. |
| 4,383,834 A | 5/1983 | Degen et al. |
| 4,423,194 A | 12/1983 | Löbach et al. |
| 4,440,597 A | 4/1984 | Wells et al. |
| 4,448,638 A | 5/1984 | Klowak |
| 4,481,076 A | 11/1984 | Herrick |
| 4,481,077 A | 11/1984 | Herrick |
| 4,482,429 A | 11/1984 | Klowak |
| 4,508,594 A | 4/1985 | Jansma et al. |
| 4,514,345 A | 4/1985 | Johnson et al. |
| 4,521,490 A | 6/1985 | Pocius et al. |
| 4,528,239 A | 7/1985 | Trokhan |
| 4,529,480 A | 7/1985 | Trokhan |
| 4,584,357 A | 4/1986 | Harding |
| 4,618,448 A | 10/1986 | Cha et al. |
| 4,695,606 A | 9/1987 | Floyd et al. |
| 4,764,418 A | 8/1988 | Kuenn et al. |
| 4,766,245 A | 8/1988 | Larkin et al. |
| 4,808,266 A | 2/1989 | Faurie |
| 4,824,689 A | 4/1989 | Kuenn et al. |
| 4,908,101 A | 3/1990 | Frisk et al. |
| 4,921,902 A | 5/1990 | Evani et al. |
| 4,929,670 A | 5/1990 | Billmers et al. |
| 4,950,545 A | 8/1990 | Walter et al. |
| 4,959,125 A | 9/1990 | Spendel |

(Continued)

FOREIGN PATENT DOCUMENTS

CA 2296826 A1 7/2000

(Continued)

OTHER PUBLICATIONS

Haylock, "Paper: Its making, merchanting and usage", $3^{rd}$ ed, The National Association of Paper Merchants, London, 1974, p. 69.*

(Continued)

*Primary Examiner*—Steven P Griffin
*Assistant Examiner*—Dennis Cordray
(74) *Attorney, Agent, or Firm*—Dority & Manning, P.A.

(57) ABSTRACT

Fibrous products containing a durable softening agent are disclosed. The softening agent generally comprises a polysiloxane containing a plurality of first functional groups. In order to improve the wet retention of the softening agent on cellulosic fibers, the softening agent is reacted with a retention agent. The retention agent generally comprises a cationic polymer having a second functional group. In one embodiment, for instance, the softening agent contains epoxy groups or anhydride groups, while the retention agent contains amine groups. Products that may be made according to the present invention include tissue products, wipes and other absorbent articles.

27 Claims, No Drawings

U.S. PATENT DOCUMENTS

| | | |
|---|---|---|
| 4,969,976 A | 11/1990 | Reed |
| 4,981,557 A | 1/1991 | Bjorkquist |
| 4,986,882 A | 1/1991 | Mackey et al. |
| 5,011,918 A | 4/1991 | Bilimers et al. |
| 5,035,772 A | 7/1991 | Agnemo et al. |
| 5,049,634 A | 9/1991 | Tsai et al. |
| 5,057,166 A | 10/1991 | Young, Sr. et al. |
| 5,059,282 A | 10/1991 | Ampulski et al. |
| 5,071,675 A | 12/1991 | Gupta et al. |
| 5,073,234 A | 12/1991 | Mollett et al. |
| 5,087,324 A | 2/1992 | Awofeso et al. |
| 5,098,522 A | 3/1992 | Smurkoski et al. |
| 5,100,956 A | 3/1992 | O'Lenick, Jr. |
| 5,127,994 A | 7/1992 | Johansson |
| 5,137,600 A | 8/1992 | Barnes et al. |
| 5,139,671 A | 8/1992 | Henricson et al. |
| 5,143,999 A | 9/1992 | Setiabudi et al. |
| 5,164,046 A | 11/1992 | Ampulski et al. |
| 5,177,165 A | 1/1993 | Valint, Jr. et al. |
| 5,187,219 A | 2/1993 | Furman, Jr. |
| 5,221,434 A | 6/1993 | Henricson |
| 5,227,242 A | 7/1993 | Walter et al. |
| 5,230,776 A | 7/1993 | Andersson et al. |
| 5,238,501 A | 8/1993 | Kappel et al. |
| 5,260,171 A | 11/1993 | Smurkoski et al. |
| 5,275,700 A | 1/1994 | Trokhan |
| 5,300,192 A | 4/1994 | Hansen et al. |
| 5,328,565 A | 7/1994 | Rasch et al. |
| 5,334,289 A | 8/1994 | Trokhan et al. |
| 5,338,407 A * | 8/1994 | Dasgupta ............... 162/168.3 |
| 5,348,620 A | 9/1994 | Hermans et al. |
| 5,353,521 A | 10/1994 | Orloff |
| 5,362,415 A | 11/1994 | Egraz et al. |
| 5,397,435 A | 3/1995 | Ostendorf et al. |
| 5,397,834 A | 3/1995 | Jane et al. |
| 5,401,810 A | 3/1995 | Jansma et al. |
| 5,405,501 A | 4/1995 | Phan et al. |
| 5,431,786 A | 7/1995 | Rasch et al. |
| 5,435,919 A | 7/1995 | Ladika et al. |
| 5,437,766 A | 8/1995 | Van Phan et al. |
| 5,494,554 A | 2/1996 | Edwards et al. |
| 5,496,624 A | 3/1996 | Stelljes, Jr. et al. |
| 5,500,277 A | 3/1996 | Trakhan et al. |
| 5,501,768 A | 3/1996 | Hermans et al. |
| 5,514,523 A | 5/1996 | Trokhan et al. |
| 5,529,665 A | 6/1996 | Kaun |
| 5,538,595 A | 7/1996 | Trokhan et al. |
| 5,547,745 A | 8/1996 | Hansen et al. |
| 5,552,020 A | 9/1996 | Smith et al. |
| 5,554,467 A | 9/1996 | Trokhan et al. |
| 5,558,873 A | 9/1996 | Funk et al. |
| 5,566,724 A | 10/1996 | Trokhan et al. |
| 5,573,637 A | 11/1996 | Ampulski et al. |
| 5,575,891 A | 11/1996 | Trokhan et al. |
| 5,580,566 A * | 12/1996 | Syverson et al. ............ 424/404 |
| 5,585,456 A | 12/1996 | Dulany et al. |
| 5,591,306 A | 1/1997 | Kaun |
| 5,598,642 A | 2/1997 | Orloff et al. |
| 5,601,871 A | 2/1997 | Krzysik et al. |
| 5,603,804 A | 2/1997 | Hansen et al. |
| 5,607,551 A | 3/1997 | Farrington, Jr. et al. |
| 5,609,727 A | 3/1997 | Hansen et al. |
| 5,612,409 A | 3/1997 | Chrobaczek et al. |
| 5,618,483 A | 4/1997 | Weigel et al. |
| 5,624,532 A | 4/1997 | Trokhan et al. |
| 5,624,676 A | 4/1997 | Mackey et al. |
| 5,624,790 A | 4/1997 | Trokhan et al. |
| 5,628,876 A | 5/1997 | Ayers et al. |
| 5,633,300 A | 5/1997 | Dasgupta |
| 5,637,194 A | 6/1997 | Ampulski et al. |
| 5,643,588 A * | 7/1997 | Roe et al. .................. 424/402 |
| 5,650,218 A | 7/1997 | Krzysik et al. |
| 5,656,132 A | 8/1997 | Farrington, Jr. et al. |
| 5,667,636 A | 9/1997 | Engel et al. |
| 5,672,248 A | 9/1997 | Wendt et al. |
| 5,674,362 A | 10/1997 | Underwood et al. |
| 5,693,411 A | 12/1997 | Hansen et al. |
| 5,695,607 A | 12/1997 | Oriaran et al. |
| 5,698,688 A | 12/1997 | Smith et al. |
| 5,723,022 A | 3/1998 | Dauplaise et al. |
| 5,725,736 A | 3/1998 | Schroeder et al. |
| 5,746,887 A | 5/1998 | Wendt et al. |
| 5,772,845 A | 6/1998 | Farrington, Jr. et al. |
| 5,783,041 A | 7/1998 | Underwood |
| 5,785,813 A | 7/1998 | Smith et al. |
| 5,788,815 A | 8/1998 | Norell et al. |
| 5,807,944 A | 9/1998 | Hirt et al. |
| 5,814,188 A | 9/1998 | Vinson et al. |
| 5,874,495 A | 2/1999 | Robinson |
| 5,885,697 A | 3/1999 | Krzysik et al. |
| 5,906,926 A | 5/1999 | Keunecke et al. |
| 5,935,383 A | 8/1999 | Sun et al. |
| 6,059,928 A | 5/2000 | Van Luu et al. |
| 6,096,169 A | 8/2000 | Hermans et al. |
| 6,103,063 A | 8/2000 | Oriaran et al. |
| 6,137,600 A | 10/2000 | Sakurai et al. |
| 6,143,135 A | 11/2000 | Hada et al. |
| 6,224,714 B1 | 5/2001 | Schroeder et al. |
| 6,228,126 B1 | 5/2001 | Cimecioglu et al. |
| 6,235,155 B1 | 5/2001 | Schroeder et al. |
| 6,235,602 B1 | 5/2001 | Yuzuriha |
| 6,267,842 B1 | 7/2001 | Ona et al. |
| 6,270,893 B1 | 8/2001 | Young, Sr. et al. |
| 6,274,667 B1 | 8/2001 | Shannon et al. |
| 6,287,418 B1 | 9/2001 | Schroeder et al. |
| 6,300,259 B1 | 10/2001 | Westland et al. |
| 6,361,651 B1 | 3/2002 | Sun |
| 6,365,667 B1 | 4/2002 | Shannon et al. |
| 6,368,456 B1 | 4/2002 | Cimecioglu et al. |
| 6,379,494 B1 | 4/2002 | Jewell et al. |
| 6,379,498 B1 | 4/2002 | Burns et al. |
| 6,398,911 B1 | 6/2002 | Schroeder et al. |
| 6,409,881 B1 | 6/2002 | Jaschinski |
| 6,423,183 B1 | 7/2002 | Goulet et al. |
| 6,432,268 B1 | 8/2002 | Burghardt |
| 6,432,270 B1 | 8/2002 | Liu et al. |
| 6,461,553 B1 | 10/2002 | Hansen et al. |
| 6,464,602 B1 | 10/2002 | Schroeder et al. |
| 6,472,487 B2 | 10/2002 | Schroeder et al. |
| 6,488,812 B2 | 12/2002 | Shannon et al. |
| 6,503,412 B1 | 1/2003 | Schroeder |
| 6,511,580 B1 | 1/2003 | Liu |
| 6,514,383 B1 | 2/2003 | Liu et al. |
| 6,517,678 B1 | 2/2003 | Shannon et al. |
| 6,521,339 B1 | 2/2003 | Hansen et al. |
| 6,528,121 B2 | 3/2003 | Ona et al. |
| 6,544,386 B1 | 4/2003 | Krzysik et al. |
| 6,547,925 B1 | 4/2003 | Drew et al. |
| 6,573,424 B1 | 6/2003 | Raidel et al. |
| 6,576,087 B1 | 6/2003 | Liu |
| 6,582,558 B1 | 6/2003 | Liu |
| 6,582,560 B2 | 6/2003 | Runge et al. |
| 6,596,126 B1 | 7/2003 | Shannon et al. |
| 6,599,393 B1 | 7/2003 | Liu |
| 6,620,295 B2 | 9/2003 | Shannon et al. |
| 6,632,904 B2 | 10/2003 | Schroeder et al. |
| 6,749,721 B2 | 6/2004 | Shannon et al. |
| 6,752,905 B2 | 6/2004 | Hu et al. |
| 6,951,598 B2 * | 10/2005 | Flugge et al. ............ 162/164.4 |
| 2002/0074098 A1 | 6/2002 | Shannon et al. |
| 2002/0134521 A1 | 9/2002 | Shannon et al. |
| 2003/0037894 A1 | 2/2003 | Shannon et al. |
| 2003/0085010 A1 * | 5/2003 | Burazin et al. ............... 162/109 |
| 2003/0136531 A1 | 7/2003 | Edwards et al. |

| | | | |
|---|---|---|---|
| 2003/0159786 A1 | 8/2003 | Runge et al. | |
| 2004/0045687 A1 | 3/2004 | Shannon et al. | |
| 2004/0084164 A1 | 5/2004 | Shannon et al. | |
| 2004/0084165 A1 | 5/2004 | Shannon et al. | |
| 2004/0086726 A1 | 5/2004 | Moline et al. | |
| 2004/0118531 A1 | 6/2004 | Shannon et al. | |
| 2004/0118533 A1 | 6/2004 | Shannon et al. | |
| 2004/0123962 A1 | 7/2004 | Shannon et al. | |
| 2004/0163785 A1* | 8/2004 | Shannon et al. | 162/158 |

FOREIGN PATENT DOCUMENTS

| | | |
|---|---|---|
| CA | 2296891 A1 | 7/2000 |
| EP | 0109282 B1 | 5/1984 |
| EP | 0226408 B1 | 6/1987 |
| EP | 0613979 A1 | 9/1994 |
| EP | 0643164 B1 | 3/1995 |
| EP | 0685593 A2 | 12/1995 |
| EP | 0685593 A3 | 12/1995 |
| EP | 0851062 A2 | 7/1998 |
| EP | 0851062 A3 | 7/1998 |
| WO | WO 8902952 A1 | 4/1989 |
| WO | WO 9012146 A1 | 10/1990 |
| WO | WO 9419534 A1 | 9/1994 |
| WO | WO 9501479 A1 | 1/1995 |
| WO | WO 9520066 A1 | 7/1995 |
| WO | WO 9606223 A1 | 2/1996 |
| WO | WO 9713026 A1 | 4/1997 |
| WO | WO 9736052 A2 | 10/1997 |
| WO | WO 9736052 A3 | 10/1997 |
| WO | WO 9809021 A1 | 3/1998 |
| WO | WO 9816570 A1 | 4/1998 |
| WO | WO 9817864 A1 | 4/1998 |
| WO | WO 9823814 A1 | 6/1998 |
| WO | WO 9835095 A1 | 8/1998 |
| WO | WO 9934057 A1 | 7/1999 |
| WO | WO 0039389 A1 | 7/2000 |
| WO | WO 0148025 A1 | 7/2001 |
| WO | WO 0231260 A2 | 4/2002 |
| WO | WO 0231260 A3 | 4/2002 |
| WO | WO 02072946 A2 | 9/2002 |
| WO | WO 02072951 A2 | 9/2002 |

OTHER PUBLICATIONS

TAPPI Official Test Method T 402 om-93, "Standard Conditioning and Testing Atmospheres For Paper, Board, Pulp Handsheets, and Related Products," published by the TAPPI Press, Atlanta, Georgia, revised 1993, pp. 1-3.

Smook, Gary A., Editor, "Non-Fibrous Additives to Papermaking Stock," Chapter 15, Handbook for Pulp & Paper Technologists, Second Edition, Angus Wilde Publications, Bellingham, WA, 1992, pp. 220, 225-226.

Article with English Abstract—*Reaktionen von Cellulose in homogener Lösung*, M. Diamantoglou and H. Kuhne, Das Papier, 42, 1988, pp. 690-696.

Article—*Ether bond crosslinking of cellulose with epichlorohydrin*, Etherification of Cellulose, pp. 243-246.

Article—*Cellulose carbamate*, D. Klemm, B. Philipp, T. Heinze, U. Heinze, and W. Wagenknecht, Comprehensive Cellulose Chemistry vol. 2, Functionalization of Cellulose, 1998, pp. 161-162.

Chapter 17 entitled "Derivatives of Cellulose" from *Wood Chemistry Ultrastructure Reactions*, D. Fengel and G. Wegener, 1983, pp. 482-525.

Article—*Preparation of acid anhydrides*, Stanley H. Pine, James B. Hendrickson, Donald J. Cram, and George S. Hammond, Organic Chemistry, $4^{th}$ Edition, p. 312.

Article—*Comparative Spectroscopic Study of the Modification of Cellulosic Materials with Different Coupling Agent*, Journal of Applied Polymer Science, vol. 75, 2000, pp. 256-266.

Article—*Ultraviolet Spectroscopic Study Of The Cellulose Functinalization With Silanes*, Spectroscopy Letters, vol. 32, No. 6, 1999, pp. 993-1003.

Article—*Copolymers of acrylamide and surfactant macromonomers: synthesis and solution properties*, D. N. Schulz, J. J. Kaladas, J. J. Maurer, J. Bock, S. J. Pace, and W. W. Schulz, Polymer, vol. 28, 1987, pp. 2110-2115.

Organic Synthesis, Collective vol. 4, *Ethanedithiol*, 1963, pp. 401-403.

Article—*The Standardization and Analysis of Hand Evaluation ($2^{nd}$ Edition)*, Sueo Kawabata, The Textile Machinery Society of Japan, Jul. 1980, pp. 28-51.

Paper Chemistry, J. C. Roberts, 1996, Blackie Academic & Professional, Glasgow XP002210178, Chapter 7, Wet-Strength Chemistry, Point 7.3.4, Glyoxalated Polyacrylamide Resins, pp. 107-110.

Search Report and Written Opinion for PCT/US2005/037277, Sep. 29, 2006.

* cited by examiner

SOFT AND DURABLE TISSUE PRODUCTS CONTAINING A SOFTENING AGENT

BACKGROUND OF THE INVENTION

Softness and flexibility are key attributes for tissue and absorbent articles. One method to enhance softness or flexibility in these products is to add a softening agent such as silicone. Typically, the softening agent is added to the pulp fibers through a pretreatment or, for some tissues, applied topically to the outer surface. When using silicone pretreated pulp in tissues, the softness gain may be further enhanced through layering the fibers. Although the softness and flexibility gain from adding silicone additives is advantageous, this class of additives tends to have incomplete retention on the fibers, tends to be hydrophobic and may cause problems with absorbency. Due to the absorbency limitations, there has been much work on developing the chemistry and application of wettable silicones. Although these alternative silicones have helped to mitigate absorbency problems, they have also aggravated the retention efficiency. For example, a portion of the wettable softening agent may desorb from the pretreated fibers when in contact with water or body fluid.

For tissue machines, the unretained softening agents are recirculated through a "short-loop" water recirculation and may contaminate other fibers, fabrics, and creping surfaces. This is especially troublesome for layered tissue products where softening agents are desired on the outer layers and strength agents are desired in the center of the product. For absorbent articles, the unretained silicone reduces surface tension and can interfere with wicking, and superabsorbent particle capacity.

Thus, a need currently exists for a method of improving the retention of softening agents on pretreated pulp. For instance, a need currently exists for a method of improving the retention of wettable silicones on cellulosic fibers used in the production of tissue products and other absorbent articles.

SUMMARY OF THE INVENTION

In general, the present disclosure is directed to soft and durable absorbent products, such as tissue products that have been treated with a softening agent. The softening agent in one embodiment, may be a polysiloxane that has been modified to decrease the hydrophobicity of the compound. In accordance with the present invention, a retention agent is used in combination with a softening agent in order to improve the retention of the softening agent on cellulosic fibers under aqueous conditions.

In forming an absorbent article, cellulosic fibers are first pretreated with the softening agent. The fibers are then used alone or in combination with other fibers to form an article, such as a tissue web. The retention agent is incorporated into the web. The retention agent reacts or otherwise associates with the softening agent causing the softening agent to crosslink, to form more durable bonds and less likely to desorb from the fibers.

In one embodiment, for instance, the present invention is directed to the production of tissue products, such as facial tissue, paper towels, industrial wipers and the like. The tissue product includes at least one tissue web containing cellulosic fibers. At least a portion of the cellulosic fibers have been pretreated with a softening agent comprising a polysiloxane containing a plurality of a first functional group. The tissue web, for instance, may have a basis weight of from about 10 gsm to about 100 gsm.

A retention agent is also incorporated into the tissue web. The retention agent comprises a polymer containing a plurality of a second functional group. The second functional group, for instance, may comprise an amine group, an amide group, an anhydride group, an aldehyde group, an epoxy group, an epihalohydrin group, or mixtures thereof. The retention agent is reacted with the polysiloxane. The retention agent is present in the tissue web in an amount sufficient to increase the retention of the polysiloxane to the cellulosic fiber by at least 10% under aqueous conditions. For instance, the retention of the polysiloxane can be increased by greater than about 50%, greater than about 100%, greater than about 200%, or even greater than about 300% under aqueous conditions. In some embodiments, the tissue product may also exhibit low slough properties and relatively high wet strength. The tissue product can also have a wet-out time of less than about 200 seconds.

In one embodiment, the polysiloxane softening agent may have the following formula:

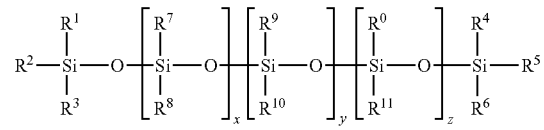

Wherein, x and z are integers $\geq 0$. y is an integer $\geq 0$, the mole ratio of x to (x+y+z) is from about 0.05 percent to about 95 percent, the ratio of y to (x+y+z) is from about 0 percent to about 25%, the $R^0$-$R^9$ moieties are independently any organofunctional group including $C_1$ or higher alkyl groups, ethers, polyethers, polyesters, amines, imines, amides, epoxy, anhydride, aldehyde, carboxylic, or epihalohydrin groups including the alkyl and alkenyl analogues of such groups, the $R^{10}$ moiety is an amino functional moiety, $R^{11}$ is a polyether functional group having the generic formula: —$R^{12}$—($R^{13}$—O)$_a$—($R^{14}$O)$_b$—$R^{15}$, wherein $R^{12}$, $R^{13}$, and $R^{14}$ are independently $C_{1-4}$ alkyl groups, linear or branched; $R^{15}$ is H or a $C_{1-30}$ alkyl group; and, "a" and "b" are integers of from about 1 to about 100.

As shown above, the first functional group contained on the polysiloxane softening agent may comprise epoxy groups, anhydride groups, amine groups, aldehyde groups, carboxylic groups, epihalohydrin groups, and mixtures thereof. Vinyl grafts of polysiloxanes may also be used. The first functional group may be contained in the polysiloxane in an amount from about 0.1 mole percent to about 75 mole percent. The polysiloxane may have a viscosity of from about 5 centipoise to about 5,000 centipoise and may be incorporated into the tissue web in an amount from about 0.1 kg/T to about 100 kg/T, such as from about 1 kg/T to about 20 kg/T.

In one particular embodiment, the first functional groups contained on the polysiloxane comprise epoxy groups, anhydride groups or mixtures thereof, and wherein the plurality of second functional groups contained upon the retention agent may comprise amine groups. In an alternative embodiment, the first functional group contained upon the polysiloxane may comprise amine groups, while the second functional group contained upon the retention agent also comprises amine groups. In this embodiment, better reaction conditions may occur if the softening agent and the retention agent contact each other under acidic conditions. For instance, the pH of the surrounding solution may be less than about 7, such as less than about 5, such as from about 3 to about 5.

In order for the softening agent to react with the retention agent, a catalyst, an energy source, or both are needed. In one embodiment, for instance, in order to react the retention agent with the softening agent, the tissue web may be heated using infrared rays, microwaves, ultrasound, plasma, steam, or any other suitable thermal source. The reaction between the retention agent and the softening agent may occur before the tissue web is dried to a final dryness or during drying of the web.

Examples of retention agents that may be used in the present invention include glyoxylated polyacrylamide resins, polyamide-polyamine-epichlorohydrin resins, polyethyleneimine resins, polyvinylamine resins, copolymers thereof, and mixtures thereof. The retention agent may be incorporated into the tissue product in an amount from about 0.1 kg/T to about 20 kg/T, such as from about 0.1 kg/T to about 10 kg/T and, in one embodiment, from about 1 kg/T to about 5 kg/T.

The tissue product may be made according to any suitable papermaking process. For instance, the tissue web may be creped or may comprise an uncreped through-air dried web. In one embodiment, the tissue web may be made from a stratified fiber furnish containing separate layers of fibers. For example, the tissue web may contain three layers of fibers. The cellulosic fibers pretreated with a softening agent may be contained solely within at least one outer layers of the web. The resulting tissue product may have a single ply or may be a multi-ply product.

In an alternative embodiment of the present invention, the pretreated cellulosic fibers may be contained in an absorbent article, such as a diaper, incontinence product, feminine napkin, and the like. In one particular embodiment, for instance, an absorbent layer may be formed in an airlaid process. The absorbent layer may contain cellulosic fibers pretreated with a polysiloxane softening agent as described above. In accordance with the present invention, a retention agent may be incorporated into the absorbent layer and reacted with the softening agent in order to improve the retention of the softening agent on the cellulosic fibers. The retention agent, for instance, may be incorporated into an aqueous solution and sprayed upon the absorbent layer. Alternatively, cellulosic fibers pretreated with the retention agent may be incorporated into the absorbent layer and then reacted with the softening agent. In order for the reaction to occur, for instance, the absorbent layer may be slightly wetted and then subjected to an energy source sufficient to cause the reaction.

When forming the airlaid webs, the cellulosic fibers may comprise fluff that is pretreated with the softening agent or the retention agent. Superabsorbent particles may also be incorporated into the absorbent web. Once the softening agent is reacted with the retention agent, the absorbent layer may be incorporated into any suitable absorbent article.

Other features and aspects of the present invention are discussed in greater detail below.

DETAILED DESCRIPTION

It is to be understood by one of ordinary skill in the art that the present discussion is a description of exemplary embodiments only, and is not intended as limiting the broader aspects of the present invention.

In general, the present disclosure is directed to a method for improving the retention of softening agents on cellulosic fibers, such as pulp fibers. The softening agent may comprise, for instance, a polysiloxane, such as a chemically modified polysiloxane that may have decreased hydrophobicity. In accordance with the present invention, cellulosic fibers may first be pretreated with a softening agent. During formation of an article containing the pretreated cellulosic fibers, the softening agent is reacted with a retention agent. The retention agent, for instance, may comprise a cationic polymer having functional groups that react with functional groups on the softening agent. Once reacted with the retention agent, the retention of the softening agent on the cellulosic fibers may be increased by at least about 10% under aqueous conditions. For instance, retention of the softening agent may increase by at least 50%, by at least 60%, by at least 70%, by at least 80%, by at least 100%, by at least 200%, or may even increase by at least 300%.

In one embodiment of the present invention, the softening agent and the retention agent are incorporated into a tissue product, such as a facial tissue, a bath tissue, a paper towel, an industrial wiper, a bandage, a medical drape, or the like. In an alternative embodiment, the softening agent and the retention agent are incorporated into other types of absorbent articles, such as a diaper, an adult incontinence product, a feminine hygiene product, and the like. When incorporated into an absorbent article as described above, the softening agent and the retention agent may be present in an absorbent structure containing, for instance, superabsorbent particles. When constructing a diaper, for instance, the diaper may include a cover layer and a liner. The absorbent structure may be positioned in between the cover layer and the liner.

The softening agent that may be used in accordance with the present invention may comprise a polysiloxane. The polysiloxane, for instance, may be modified to include a first functional group. The functional group, for instance, may comprise epoxy groups, anhydride groups, amine groups, aldehyde groups, carboxylic groups, epihalohydrin groups, and mixtures thereof. Vinyl grafts of polysiloxanes may also be used. As described above, cellulose fibers are pretreated with the above softening agents. A retention agent is then reacted with the softening agent to improve wet retention of the softening agent on the cellulose fibers. The retention agent may, for instance, comprise a cationic polymer containing a second functional group. The second functional group, for example, may comprise amine groups, amide groups, anhydride groups, aldehyde groups, epoxy groups, epihalohydrin groups, and mixtures thereof.

In one particular embodiment of the present invention, the first functional groups on the polysiloxane comprise epoxy groups or anhydride groups, while the second functional groups contained on the retention agent comprise amine groups. In another embodiment of the present invention, both the first functional group on the softening agent and the second functional group on the retention agent comprise amine groups.

As will be described in more detail below, the cellulose fibers pretreated with the softening agent may be contacted with the retention agent in various ways in forming absorbent articles including tissue products. Once the cellulose fibers pretreated with the softening agent is contacted with the retention agent, the softening agent and the retention agent, in many embodiments, need to be subjected to an energy source in order to cause a reaction to occur between the two polymers. The energy source, for instance, may comprise thermal energy. Although unknown, it is believed that a chemical linkage forms between the first functional groups on the softening agent and the second functional groups on the retention agent. For example, although unknown, a covalent bond may form between the softening agent on the cellulose fibers and the retention agent. Other bonds, however, may form including other physiochemical bonds, hydrogen bonds and the like between the softening agent and the retention agent. Ultimately, it is believed that some type of network forms that prevents the softening agent from being released from the cellulosic fibers even in the presence of water.

As described above, the softening agent generally comprises a polysiloxane containing various functional groups. The particular polysiloxane used in the present invention may vary depending upon the particular application and desired result. Acceptable polysiloxanes are characterized in having a backbone structure as follows:

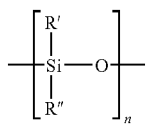

where R' and R" can be a broad range of organo and non-organo groups including mixtures of such groups and where n is an integer $\geq 2$. These polysiloxanes may be linear, branched or cyclic. They include a wide variety of polysiloxane copolymers containing various compositions of functional groups, hence, R' and R" actually may represent many different types of groups within the same polymer molecule. The organo or non-organo groups may be capable of reacting with cellulose to covalently, ionically or hydrogen bond the polysiloxane to the cellulose and also may react with the retention agent of the present invention. These functional groups may also be capable of reacting with themselves to form crosslinked matrixes with the cellulose. The scope of the invention should not be construed as limited by a particular polysiloxane structure so long as that polysiloxane structure delivers a softness attribute.

A specific class of polysiloxanes suitable for the invention has the general formula:

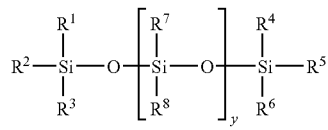

Wherein the $R^1$-$R^8$ moieties can be independently any organofunctional group including $C_1$ or higher alkyl groups, ethers, polyethers, polyesters, amines, imines, amides, epoxy, anhydride, aldehyde, carboxylic, epihalohydrin, or other functional groups including the alkyl and alkenyl analogues of such groups and y is an integer >1.

Functionalized polysiloxanes and their aqueous emulsions are well known commercially available materials. Polysiloxanes having the following structure are well suited for the purposes of the present invention and are well known in the art and readily available:

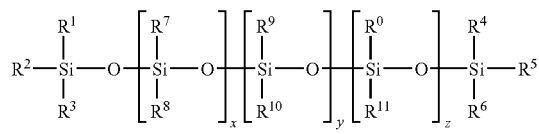

Wherein, x and z are integers $\geq 0$. y is an integer $\geq 0$. The mole ratio of x to (x+y+z) can be from about 0.05 percent to about 95 percent. The ratio of y to (x+y+z) can be from about 0 percent to about 25%. The $R^0$-$R^9$ moieties can be independently any organofunctional group including C, or higher alkyl groups, ethers, polyethers, polyesters, amines, imines, amides, epoxy, anhydride, aldehyde, carboxylic, epihalohydrin, or other functional groups including the alkyl and alkenyl analogues of such groups. The $R^{10}$ moiety is an amino functional moiety including but not limited to primary amine, secondary amine, tertiary amines, quaternary amines, unsubstituted amides and mixtures thereof. An exemplary $R^{10}$ moiety contains one amine group per constituent or two or more amine groups per substituent, separated by a linear or branched alkyl chain of $C^1$ or greater. $R^{11}$ is a polyether functional group having the generic formula: $-R^{12}-(R^{13}-O)_a-(R^{14}O)_b-R^{15}$, wherein $R^{12}$, $R^{13}$, and $R^{14}$ are independently $C_{1-4}$ alkyl groups, linear or branched; $R^{15}$ can be H or a $C_{1-30}$ alkyl group; and, "a" and "b" are integers of from about 1 to about 100, more specifically from about 5 to about 30. Exemplary aminofunctional polysiloxanes are the Wetsoft CTW family manufactured and sold by Wacker, Inc. Exemplary epoxy polysiloxanes are the Sipell family (RE 35 F and RE 63 F) and anhydride polysiloxanes are the IM 86 family, both manufactured and sold by Wacker Inc. Other exemplary polysiloxanes can be found in U.S. Pat. No. 6,432,270 by Liu, et. al.

In accordance with the present invention, cellulose fibers such as pulp fibers are pretreated with the softening agents described above. Softening agents that are particularly well suited for pretreating fibers in accordance with the present invention have epoxy functional groups, anhydride functional groups, and/or amine functional groups. In one embodiment, the softening agent is adsorbed onto the cellulose fibers without reacting the softening agent with any of the fibers. Partial surface coverage of the polysiloxane on the fiber is typically targeted. One efficient way to pretreat cellulose fibers is by drippling the polysiloxane during or after the dry-lap production of the fibers. The treated fibers may be aged at ambient temperature at least a week to ensure optimal distribution of the polysiloxane on the fibers and maximum retention through dipole and vanderWaals forces. The cellulose fibers pretreated with the polysiloxane are repulped into a fibrous suspension and possibly blended with some other untreated fibers in forming an article of the present invention.

As used herein, pretreated fibers refer to fibers that have been pretreated with, for instance, a softening agent prior to any process step that is used to form an absorbent layer, such as a tissue layer. As described above, for instance, pretreated fibers are treated with a softening agent and then dried prior to being used in the production of any fibrous articles. The fibers that are pretreated in accordance with the present invention may comprise any suitable cellulose fibers, including any suitable papermaking fiber. The fibers prior to being pretreated do not need to be chemically modified in any manner prior to contact with the softening agent.

The cellulose fibers pretreated with the softening agent according to the present invention should have a sufficient concentration of reactive sites to ensure the efficient and sufficient reaction with the retention agent in order to improve wet retention and yield high softness characteristics. For example, the softening agent may contain the first functional groups in an amount from about 0.1 mole percent to about 75 mole percent, such as from about 1 mole percent to about 50 mole percent. The mole percent of the functional groups on the softening agent may depend upon the particular softening agent used in the process. For example, the mole percent may vary from about 0.1 mole percent to about 5 mole percent or from about 10 mole percent to about 20 mole percent.

When the softening agent comprises a polysiloxane, the polysiloxane may be selected so as to have sufficient molecular weight to ensure good retention on the cellulose fibers and tissue softness while being low enough to ensure easy processability. For example, the molecular weight of polysiloxanes used in the present invention may have a viscosity ranging from about 5 centipoise to about 5,000 centipoise.

The amount of softening agent incorporated into the cellulose fibers may also vary depending upon the desired result. In general, the polysiloxane may be contacted with the cellulose fibers in an amount from about 0.1 kg/T to about 100 kg/T, such as from about 1 kg/T to about 20 kg/T. For example, in one particular embodiment, a polysiloxane containing functional groups may be used that contacts the cellulose fibers in amounts from about 3 kg/T to about 10 kg/T.

As described above, retention agents that may be used in the present invention generally include cationic polymers that contain a functional group. The functional group may comprise amine groups, amide groups, anhydride groups, aldehyde groups, epoxy groups, epihalohydrin groups, and mixtures thereof.

Retention agents that are particularly well suited for use in the present invention include glyoxylated polyacrylamide resins, polyamide-polyamine-epichlorohydrin resins, polyethyleneimine resins, polyvinylamine resins, copolymers thereof, and mixtures thereof.

Exemplary commercially available compounds include PAREZ™ 631 NC and PAREZ® 725 resins that are cationic glyoxalated polyacrylamides available from Cytec Industries (West Paterson, N.J.). These and similar resins are described in U.S. Pat. No. 3,556,932 to Coscia et al. and U.S. Pat. No. 3,556,933 to Williams et al. HERCOBOND 1366 manufactured by Hercules, Inc. (Wilmington, Del.) is another commercially available cationic glyoxalated polyacrylamide that can be used according to the present invention. Polyamide-polyamine-epichlorohydrin type resins such as KYMENE 557H are sold by Hercules, Inc. (Wilmington, Del.). Such materials have been described in patents issued to Keim (U.S. Pat. Nos. 3,700,623 and 3,772,076), Petrovich (U.S. Pat. Nos. 3,855,158; 3,899,388; 4,129,528 and 4,147,586) and van Eenam (U.S. Pat. No. 4,222,921). Poly(vinylamine-vinylformamide)[PVAm] copolymers are sold by BASF under the CATIOFAST trade name. Other cationic resins include polyethylenimine resins and aminoplast resins obtained by reaction of formaldehyde with melamine or urea.

The amount of retention agent added to the cellulose fibers in accordance with the present invention may vary depending upon the retention agent selected, the softening agent present on the fibers, the amount of the softening agent present on the fibers, and various other factors. In general, for instance, the retention agent may be added to the fibers in an amount from about 0.1 kg/T to about 20 kg/T, such as from about 0.1 kg/T to about 10 kg/T. In one particular embodiment, for instance, the retention agent may be added to the fibers in an amount from about 1 kg/T to about 5 kg/T.

The manner in which the retention agent is contacted with the softening agent in the presence of the cellulose fibers can vary depending upon the type of product being formed. In one embodiment, for instance, the retention agent and the softening agent may be added to the dry-lap pulp during the pulp manufacturing process either in the wet-end stock or the formed sheet prior to being dried.

In another embodiment, cellulosic fibers pretreated with a softening agent may be combined with cellulose fibers pretreated with the retention agent to produce a fibrous product in accordance with the present invention. Once the article is formed or during formation of the article, the mixture of cellulose fibers may be contacted with water or an aqueous solution and then subjected to an energy source sufficient for the retention agent to react with the softening agent. When forming airlaid webs, for instance, the fibrous layer containing the mixture of the pretreated cellulose fibers may be sprayed with water and then heated in order to cause the reaction to occur between the softening agent and the retention agent.

When forming tissue webs according to a wetlay process, the tissue web can at least partially be made from cellulose fibers pretreated with the softening agent. The retention agent can then be incorporated into the tissue web at any time prior to drying the web. For example, in one embodiment, the retention agent may be added to an aqueous suspension of fibers containing cellulose fibers pretreated with the softening agent. The aqueous suspension can then be deposited onto a forming surface in forming a tissue web.

In an alternative embodiment, the retention agent may be topically applied to a wet tissue web containing cellulose fibers pretreated with a softening agent. The retention agent, for instance, may be sprayed onto the wet web or printed onto the wet web using any suitable printing technique. Examples of suitable printing techniques include rotogravure printing, flexographic printing, inkjet printing, and the like. As described above, an energy source is typically needed in order to react the softening agent with the retention agent. When forming wetlaid tissue webs, the energy source needed for the reaction can be supplied from the dryer in the process which may be, for instance, a through-air dryer or a heated drum. In alternative embodiments, however, the process may be configured so that the reaction occurs prior to drying the tissue web. For instance, prior to the dryer, the process may include an energy device for supplying sufficient amounts of the energy for the reaction to occur. The energy may be supplied in the form of thermal energy, infrared energy, microwaves, ultrasound, plasma, steam, and the like.

When forming airlaid webs according to the present invention, the retention agent may also be topically applied to an airlaid web containing cellulosic fibers pretreated with the softening agent. The retention agent, for instance, may be supplied in the form of a solution and sprayed or printed on the web. After being applied to the airlaid web, an energy source as described above may be used to initiate the chemical reaction between the softening agent and the retention agent.

In some applications, better results may be obtained if the softening agent is contacted with the retention agent under acidic conditions. For instance, the pH of the environment when the softening agent contacts the retention agent may be less than about 7, such as less than about 5. For example, in one embodiment, the pH of the environment may be from about 3 to about 5. In order to reduce the pH of the environment during contact between the softening agent and the retention agent, for instance, the retention agent may be applied to the web or to an aqueous suspension of fibers in an acidic solution. Alternatively, an acidic solution may be applied to the fibrous web after the softening agent and retention agent have been added to the web. Reducing the pH as described above has been found to be especially effective when the functional groups on the softening agent and the functional groups on the retention agent are both amine groups.

Various different types of products and articles may be made in accordance with the present invention containing cellulose fibers treated with the reaction product of the softening agent and the retention agent. For example, in one embodiment, the present invention is directed to the formation of tissue products, such as facial tissue, bath tissue and paper towels. The tissue products can have a basis weight, for instance, from about 6 gsm to about 100 gsm or greater. For example, in one embodiment, the tissue product can have a basis weight of from about 10 gsm to about 100 gsm. Facial tissues, for instance, typically have a basis weight of from about 10 gsm to about 40 gsm. Paper towels, on the other hand, typically have a basis weight of from about 35 gsm to about 80 gsm.

Tissue products incorporating the chemical additives of the present invention may be made by any suitable process. Tissue products incorporated with a chemical additive in accordance with the present invention may be made by any suitable process. For the tissue sheets of the present invention, both creped and uncreped methods of manufacture may be used. Uncreped tissue production is disclosed in U.S. Pat. No. 5,772,845, issued on Jun. 30, 1998 to Farrington, Jr. et al., the disclosure of which is herein incorporated by reference to the extent it is non-contradictory herewith. Creped tissue production is disclosed in U.S. Pat. No. 5,637,194, issued on Jun. 10, 1997 to Ampulski et al.; U.S. Pat. No. 4,529,480, issued on Jul. 16, 1985 to Trokhan; U.S. Pat. No. 6,103,063, issued on Aug. 15, 2000 to Oriaran et al.; and, U.S. Pat. No. 4,440,597, issued on Apr. 3, 1984 to Wells et al., the disclosures of all of which are herein incorporated by reference to the extent that they are non-contradictory herewith. Also suitable for application of the above mentioned chemical additives are tissue sheets that are pattern densified or imprinted, such as the webs disclosed in any of the following U.S. Pat. No. 4,514,345, issued on Apr. 30, 1985 to Johnson et al.; U.S. Pat. No. 4,528,239, issued on Jul. 9, 1985 to Trokhan; U.S. Pat. No. 5,098,522, issued on Mar. 24, 1992; U.S. Pat. No. 5,260,171, issued on Nov. 9, 1993 to Smurkoski et al.; U.S. Pat. No. 5,275,700, issued on Jan. 4, 1994 to Trokhan; U.S. Pat. No. 5,328,565, issued on Jul. 12, 1994 to Rasch et al.; U.S. Pat. No. 5,334,289, issued on Aug. 2, 1994 to Trokhan et al.; U.S. Pat. No. 5,431,786, issued on Jul. 11, 1995 to Rasch et al.; U.S. Pat. No. 5,496,624, issued on Mar. 5, 1996 to Steltjes, Jr. et al.; U.S. Pat. No. 5,500,277, issued on Mar. 19, 1996 to Trokhan et al.; U.S. Pat. No. 5,514,523, issued on May 7, 1996 to Trokhan et al.; U.S. Pat. No. 5,554,467, issued on Sep. 10, 1996 to Trokhan et al.; U.S. Pat. No. 5,566,724, issued on Oct. 22, 1996 to Trokhan et al.; U.S. Pat. No. 5,624,790, issued on Apr. 29, 1997 to Trokhan et al.; and, U.S. Pat. No. 5,628,876, issued on May 13, 1997 to Ayers et al., the disclosures of all of which are herein incorporated by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits is deflected by an air pressure differential across the deflection conduit to form a lower-density pillow-like region or dome in the tissue sheet.

Various drying operations may be useful in the manufacture of the tissue products of the present invention. Examples of such drying methods include, but are not limited to, drum drying, through drying, steam drying such as superheated steam drying, displacement dewatering, Yankee drying, infrared drying, microwave drying, radiofrequency drying in general, and impulse drying, as disclosed in U.S. Pat. No. 5,353,521, issued on Oct. 11, 1994 to Orloff and U.S. Pat. No. 5,598,642, issued on Feb. 4, 1997 to Orloff et al., the disclosures of both which are herein incorporated by reference to the extent that they are non-contradictory herewith. Other drying technologies may be used, such as methods employing differential gas pressure include the use of air presses as disclosed U.S. Pat. No. 6,096,169, issued on Aug. 1, 2000 to Hermans et al. and U.S. Pat. No. 6,143,135, issued on Nov. 7, 2000 to Hada et al., the disclosures of both which are herein incorporated by reference to the extent they are non-contradictory herewith. Also relevant are the paper machines disclosed in U.S. Pat. No. 5,230,776, issued on Jul. 27, 1993 to I. A. Andersson et al. The tissue product may contain a variety of fiber types, in addition to the modified cellulose, both natural and synthetic. In one embodiment the tissue product comprises hardwood and softwood fibers. The overall ratio of hardwood pulp fibers to softwood pulp fibers within the tissue product, including individual tissue sheets making up the product may vary broadly. The ratio of hardwood pulp fibers to softwood pulp fibers may range from about 9:1 to about 1:9, more specifically from about 9:1 to about 1:4, and most specifically from about 9:1 to about 1:1. In one embodiment of the present invention, the hardwood pulp fibers and softwood pulp fibers may be blended prior to forming the tissue sheet thereby producing a homogenous distribution of hardwood pulp fibers and softwood pulp fibers in the z-direction of the tissue sheet. In another embodiment of the present invention, the hardwood pulp fibers and softwood pulp fibers may be layered so as to give a heterogeneous distribution of hardwood pulp fibers and softwood pulp fibers in the z-direction of the tissue sheet. In another embodiment, the hardwood pulp fibers may be located in at least one of the outer layers of the tissue product and/or tissue sheets wherein at least one of the inner layers may comprise softwood pulp fibers. In still another embodiment the tissue product contains secondary or recycled fibers optionally containing virgin or synthetic fibers.

In addition, synthetic fibers may also be utilized in the present invention. The discussion herein regarding pulp fibers is understood to include synthetic fibers. Some suitable polymers that may be used to form the synthetic fibers include, but are not limited to: polyolefins, such as, polyethylene, polypropylene, polybutylene, and the like; polyesters, such as polyethylene terephthalate, poly(glycolic acid) (PGA), poly (lactic acid) (PLA), poly(β-malic acid) (PMLA), poly(ε-caprolactone) (PCL), poly(ρ-dioxanone) (PDS), poly(3-hydroxybutyrate) (PHB), and the like; and, polyamides, such as nylon and the like. Synthetic or natural cellulosic polymers, including but not limited to: cellulosic esters; cellulosic ethers; cellulosic nitrates; cellulosic acetates; cellulosic acetate butyrates; ethyl cellulose; regenerated celluloses, such as viscose, rayon, lyocel and the like; cotton; flax; hemp; and mixtures thereof may be used in the present invention. The synthetic fibers may be located in one or all of the layers and sheets comprising the tissue product.

When the tissue web contains a layered configuration, the synthetic fibers may be located in either the layer containing the treated fibers, the layer containing the untreated fibers or both.

When forming tissue webs from a stratified fiber furnish in order to form fibrous layers within the web as described above, the softening agent, for instance, may be contained in at least one of the outer layers of the web. For example, in a three-layered web, the softening agent may be contained in one or both outer layers.

Tissue products made according to the present invention may comprise one ply products or multiple ply products. For instance, tissue products according to the present invention may contain two plies or three plies. When containing multiple plies, the softening agent may be present in the outer plies in order to make the softening agent available at the exterior surfaces of the product.

In addition to tissue products, absorbent articles may also be produced according to the present invention containing a fibrous layer that includes the polysiloxane-treated cellulose fibers. The absorbent articles may include, for instance, diapers, incontinence products, feminine napkins, and moist wipe products. Diapers, for instance, typically include an absorbent structure positioned between a cover layer and a liner. The absorbent structure may contain the treated cellulosic fibers made in accordance with the present invention.

When forming absorbent articles as described above, the fibrous layer made according to the present invention may comprise an airformed layer. Airformed layers typically contain cellulosic fibers in the form of pulp fluff. The pulp fluff may be pretreated with the softening agent. In accordance with the present invention, the softening agent may then be reacted with the retention agent according to any of the methods described above.

When forming products according to the present invention, various optional chemical additives may be incorporated into the product as desired. The following materials are included as examples of additional chemicals that may be applied to the web containing the treated fibers of the present invention. The chemicals are included as examples and are not intended to limit the scope of the invention. Such chemicals may be added at any point in the web making process.

Additional types of chemicals that may be added to the fibers for other benefits include, but is not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin E, lotions and the like may also be incorporated into the finished products.

In general, the products of the present invention can be used in conjunction with any known materials and chemicals that are not antagonistic to its intended use. Examples of such materials include, but are not limited to, odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, humectants, emollients and the like.

The present invention may be better understood with respect to the following examples.

EXAMPLES

The following test methods were used for the present examples.

Preparation of Pulp Slurry

To prepare a pulp slurry, 24 grams (oven-dry basis) of pulp fibers were soaked in 2 liters of deionized water for 5 minutes. The pulp slurry was disintegrated for 5 minutes in a British disintegrator. The slurry was then diluted with water to a volume of 8 liters. The chemical additives were then added to the slurry. The slurry was mixed with a standard mechanical mixer at moderate shear for 5 minutes after addition of the chemical additives.

Preparation of Handsheets

Handsheets were made with a basis weight of 60 g/m$^2$ (gsm). During handsheet formation, the appropriate amount of fiber (0.3% consistency) slurry required to make a 60 gsm sheet was measured into a graduated cylinder. The slurry was then poured from the graduated cylinder into an 8.5-inch by 8.5-inch Valley handsheet mold (Valley Laboratory Equipment, Voith, Inc.) that had been pre-filled to the appropriate level with water. After pouring the slurry into the mold, the mold was then completely filled with water, including water used to rinse the graduated cylinder. The slurry was then agitated gently with a standard perforated mixing plate that was inserted into the slurry and moved up and down seven times, then removed. The water was then drained from the mold through a wire assembly at the bottom of the mold that retained the fibers to form an embryonic web. The forming wire was a 90 mesh, stainless-steel wire cloth. The web was couched from the mold wire with two blotter papers placed on top of the web with the smooth side of the blotter contacting the web. The blotters were removed and the embryonic web was lifted with the lower blotter paper, to which it was attached. The lower blotter was separated from the other blotter, keeping the embryonic web attached to the lower blotter. The blotter was positioned with the embryonic web face up, and the blotter was placed on top of two other dry blotters. Two more dry blotters were also placed on top of the embryonic web. The stack of blotters with the embryonic web was placed in a Valley hydraulic press and pressed for one minute with 100 psi applied to the web. The pressed web was removed from the blotters and placed on a Valley steam dryer containing steam at 2.5 psig pressure and heated for 2 minutes, with the wire-side surface of the web next to the metal drying surface and a felt under tension on the opposite side of the web. Felt tension was provided by a 17.5 lbs of weight pulling downward on an end of the felt that extends beyond the edge of the curved metal dryer surface. The dried handsheet was trimmed to 7.5 inches square with a paper cutter and then weighed in a heated balance with the temperature maintained at 105° C. to obtain the oven dry weight of the web. The handsheets were then subjected to dry and wet tensile testing.

Tensile Testing

Unless otherwise specified, tensile strengths are measured according to Tappi Test Method T 494 om-88 for tissue, modified in that a tensile tester is used having a 3-inch jaw width, a jaw span of 4 inches, and a crosshead speed of 10 inches per minute. Wet strength is measured in the same manner as dry strength except that the tissue sample is folded without creasing about the midline of the sample, held at the ends, and dipped in deionized water for about 0.5 seconds to a depth of about 0.5 cm to wet the central portion of the sample, whereupon the wetted region is touched for about 1 second against an absorbent towel to remove excess drops of fluid, and the sample is unfolded and set into the tensile tester jaws and immediately tested. The sample is conditioned under TAPPI conditions (50% RH, 22.7.degree. C.) before testing. Generally 5 samples are combined for wet tensile testing to ensure that the load cell reading is in an accurate range.

Tensile strength

Tissue tensile strength was reported as "GMT" (grams per 3 inches of a sample), which is the geometric mean tensile strength and is calculated as the square root of the product of machine direction (MD) tensile strength and cross-machine direction (CD) tensile strength. MD and CD tensile strengths were determined using a MTS/Sintech tensile tester (available from the MTS Systems Corp., Eden Prairie, Minn.). Tissue samples measuring 3 inch wide were cut in both the machine and cross-machine directions. For each test, a sample strip was placed in the jaws of the tester, set at a 4 inch gauge length for facial tissue and 2 inch gauge length for bath tissue. The crosshead speed during the test was 10 in./minute. The tester was connected to a computer loaded with data acquisition system; e.g., MTS TestWork for windows software. Readings were taken directly from a computer screen readout at the point of rupture to obtain the tensile strength of an individual sample.

Tensile index (TI) is a measure of tensile strength normalized for basis weight of the web tested in both dry and wet states. Tensile strength may be converted to tensile index by converting tensile strength determined in units of grams of force per 3 inches to units of Newtons per meter and dividing the result by the basis weight in grams per square meter of the tissue, to give the tensile index in Newton-meters per gram (Nm/g).

Wet/Dry TI Ratio (% Wet/Dry TI) is the wet TI divided by the dry TI multiplied by 100.

Elastic Modulus $E(kg_f)$ is the elastic modulus determined in the dry state and is expressed in units of kilograms of force. Tappi conditioned samples with a width of 3 inches are placed in tensile tester jaws with a gauge length (span between jaws) of 2 inches. The jaws move apart at a crosshead speed of 25.4 cm/min and the slope is taken as the least squares fit of the data between stress values of 50 grams of force and 100 grams of force, or the least squares fit of the data between stress values of 100 grams of force and 200 grams of force, whichever is greater. If the sample is too weak to sustain a stress of at least 200 grams of force without failure, an additional ply is repeatedly added until the multi-ply sample may withstand at least 200 grams of force without failure.

Slough

In order to determine the abrasion resistance or tendency of the fibers to be rubbed from the web when handled, each sample was measured by abrading the tissue specimens via the following method. This test measures the resistance of tissue material to abrasive action when the material is subjected to a horizontally reciprocating surface abrader. All samples were conditioned at 23° C.+/−1° C. and 50%+/−2% relative humidity for a minimum of 4 hours. The test equipment is also shown and described in U.S. Pat. No. 6,752,905.

The abrading spindle contained a stainless steel rod, 0.5" in diameter with the abrasive portion consisting of a 0.005" deep diamond pattern extending 4.25" in length around the entire circumference of the rod. The spindle was mounted perpendicularly to the face of the instrument such that the abrasive portion of the rod extends out its entire distance from the face of the instrument. Guide pins with magnetic clamps are located on each side of the spindle, one movable and one fixed, spaced 4" apart and centered about the spindle. The movable clamp and guide pins were allowed to slide freely in the vertical direction, the weight of the jaw providing the means for insuring a constant tension of the sample over the spindle surface.

Using a die press with a die cutter, the specimens were cut into 3"+/−0.05" wide×8" long strips with two holes at each end of the sample. For the tissue samples, the MD direction corresponds to the longer dimension. Each test strip was then weighed to the nearest 0.1 mg. Each end of the sample was slid onto the guide pins and magnetic clamps held the sheet in place. The movable jaw was then allowed to fall providing constant tension across the spindle.

The spindle was then moved back and forth at an approximate 15 degree angle from the centered vertical centerline in a reciprocal horizontal motion against the test strip for 40 cycles (each cycle is a back and forth stroke), at a speed of 80 cycles per minute, removing loose fibers from the web surface. Additionally, the spindle rotated counter clockwise (when looking at the front of the instrument) at an approximate speed of 5 RPMs. The magnetic clamp was then removed from the sample and the sample was slid off of the guide pins and any loose fibers on the sample surface are removed by blowing compressed air (approximately 5-10 psi) on the test sample. The test sample was then weighed to the nearest 0.1 mg and the weight loss calculated. Ten test samples per tissue sample were tested and the average weight loss value in milligrams was recorded.

Wet-Out Time

A 50 µL distilled water droplet was placed on a tissue placed on a flat glass surface, and the time required for the droplet to completely disappear was measured. The wet-out time reported is the average of 5 measurements. Prior to measurement, the tissue is equilibrated at least 4 hours at 25° C. and 50% relative humidity.

Silicone Retention by GC $BF_3$

Siloxane compound contents of samples were measured by gas chromatography after derivitization with boron triflouride diethy etherate. The procedure starts by measuring out 0.1000±0.0010 g of the cellulose sample containing the siloxane compound to the nearest 0.1 mg into 20 mL headspace vials. 100 µL of boron triflouride diethy etherate is added to the vial. After reacting for one hour the headspace of the vial is analyzed for $Me_2SiF_2$ by gas chromatography (GC). The GC system used is a Hewlett-Packard Model 5890 with a Hewlett-Packard 7964 autosampler and a flame ionization detector. A GSQ column (30 m×0.53 mm i.d.) was used, available from J&W Scientific (catalog # 115-3432). The GC system used helium as the carrier gas at a flow rate of 16.0 mL through the column and 14 mL make-up at the detector. The injector temperature was 150° C. and the detector temperature was 220° C. The chromatography conditions were 50° C. for minutes with a ramp of 10° C./minutes to 150° C. This final temperature was held for 5 minutes. The retention time for the dimethyl-diflouro-silicon was 7 minutes.

Calibration samples were prepared by treating control samples with a known amount of siloxane sample. A suitable solvent was used to make up a diluted solution of the siloxane compound. This solvent was then removed prior to derivitization by heating in an oven. The calibration standards were used to prepare a linear fit of siloxane amount versus GC detector analyte peak area. This curve was then used to determine the amount of analyte in the unknown sample, which was then converted into a percent add-on of the siloxane compound by dividing by the weight of the tissue.

Example 1

A soft and durable creped tissue made of reactive silicone pretreated fibers was reacted with an amine containing polymer used as a retention agent.

A dry lap fiber web was made at a basis weight of 180 g/m² (dry base) and dried to a solid content ranging from 75% to 100% by blending 90% (wt) Aracruz eucalyptus fibers blended with 10% softwood fibers. An epoxy end capped silicone, Sipell RE 35 F or an anhydride silicone IM86, both obtained from Wacker Chemical Corp., was dribbled on this dry fiber lab after the drying stage at a dosage of 10.8 Kg silicone/Ton fibers. The silicone pretreated dry lap was aged at least a week at room temperature.

A series of creped layered facial basesheets were made with a 32.5% eucalyptus/35% softwood fibers/32.5% eucalyptus fiber split at a basis weight of 15.6 g/m². The reactive silicone pretreated fibers, when present, were blended at 50% with untreated eucalyptus fibers in the tissue outer layers. To some of the samples a softening agent, Prosoft TQ-1003 from Hercules, Wilington was added at 1 Kg/T in the tissue outer layers. Kymene, obtained from Hercules, Wilmington Del., was added at 2 Kg/T in all tissues layers, which comprises a polyamide-polyamine-epichlorohydrin resin. Parez N.C. 631, a glyoxylated polyacrylamide, obtained from Cytec Industries (West Paterson, N.J.), was added at 0.9 Kg/T in the middle tissue layer. Two plies of tissue were calendered and folded before testing.

Sample 1 was produced without any reactive silicone additive but with the retention agents.

Sample 2 was produced without any reactive silicone additive but with the addition of Prosoft TQ-1003 and the retention agents.

Sample 3 was produced with epoxy end capped reactive silicone treated fibers blended in the outer layers reacted with the retention agent.

Sample 4 was made with anhydride reactive silicone treated fibers blended in the outer layers reacted with the retention agent.

The samples were tested for properties of facial tissues made with Reactive Silicone Pretreated Fibers and wet-end addition of amine containing polymers used as retention agents. Testing was done on the tensile properties, slough and wet-out time. The following results were obtained.

| Sample | GMT (g/3") | Slough (mg) | Wet-out time (s) | Wet CD (g/3") |
|---|---|---|---|---|
| 1 (control) | 795 | 15.4 | 4 | 207 |
| 2 (control) | 686 | 16.0 | 3 | 203 |
| 3 | 682 | 6.1 | 84 | 223 |
| 4 | 820 | 12.5 | 8 | — |

As shown above, the tissue products made according to the present invention exhibited decreased slough in relation to the control samples while maintaining comparable strength. As shown above, Sample 3 made in accordance with the present invention also exhibited higher wet strength in comparison to the controls.

Example 2

Handsheets were constructed with functionalized silicone pretreated fibers reacted with a retention agent and tested for silicone retention, tensile index, wet-out time, slough, wet/dry tensile index (%), elastic modulus, and wet tensile index.

An eucalyptus drylap pulp sheet available from Aracruz, Brasil, was pretreated with 1% (wt) functionalized silicone and aged 48 hours at ambient conditions. Handsheets were constructed using the standard method described above. Retention agents were incorporated into the handsheets. In particular, amine containing polyelectrolytes, such as KYMENE 6500 (polyamide-polyamine-epichlorohydrin resin), obtained from Hercules, Wilmington Del. ("kymene") and CATIOFAST VFH (polyvinylamine) obtained from BASF, Ludwigshafen Germany ("PVam"), were used in the wet-end at 5 Kg/T. The polymers were mixed 5 minutes with the thick stock (50 g fibers in 8 L water) prior to handsheet making. In some cases, additional heat was provided by submitting the handsheets 30 seconds at 160° C. using a through-air-dried (TAD).

The handsheets were measured in tension (wet and dry) and silicone retention was analyzed by chromatographic techniques (GC $BF_3$), both methods described above. Pulp fibers were pretreated with 4 reactive silicones, all obtained from Wacker Chemical Corp.

Samples 5-9 were not pretreated with any reactive silicones.

Samples 10-13 were pretreated with Sipell RE 35F, an end-capped epoxy silicone.

Samples 14-17 were pretreated with Sipell RE 63 F, a silicone with epoxy functionalities in the backbone.

Samples 18-21 were pretreated with IM-86, an anhydride silicone.

Samples 22-24 were pretreated with 22254 VP, an epoxy-glycol modified silicone oil.

The following results were obtained:

| Sample | Retention Agent | Cured | Silicone retention (%) | Wet out Time (s) | Slough (mg) | E (Kgf) | Wet TI (Nm/g) | Dry TI (Nm/g) | Wet/dry TI (%) |
|---|---|---|---|---|---|---|---|---|---|
| 5 | None | | 0 | 3 | 16.4 | 333 | 0.6 | 10.0 | 6 |
| 6 | Pvam | | 0 | 3 | 16.5 | 428 | 1.9 | 14.9 | 12 |
| 7 | None | Yes | — | 2 | 17 | 322 | 0.6 | 9.8 | 6 |
| 8 | Pvam | Yes | — | 4 | 8 | 400 | 2.0 | 14.9 | 13 |
| 9 | Kymene | | 0 | — | — | — | — | 16.6 | — |
| 10 | None | | 24 | — | — | — | — | 8.0 | — |
| 11 | Pvam | | 72 | 600 | 9.5 | 343 | 5.0 | 10.5 | 47 |
| 12 | Pvam | Yes | — | 600 | 8 | 338 | 5.4 | 10.9 | 49 |
| 13 | Kymene | | 60 | — | — | — | — | 11.8 | — |
| 14 | None | | 24 | — | — | — | — | 7.0 | — |
| 15 | Pvam | | 66 | 600 | 10.6 | 335 | 4.2 | 10.4 | 40 |
| 16 | Pvam | Yes | — | 600 | 10.3 | 329 | 5.1 | 10.5 | 48 |
| 17 | Kymene | | 68 | — | — | — | — | 12.2 | — |
| 18 | None | | 72 | — | — | — | — | 6.5 | — |
| 19 | Pvam | | 80 | 36 | 9.1 | 381 | 2.3 | 10.6 | 22 |
| 20 | Pvam | Yes | 80 | 330 | 7.9 | 309 | 2.7 | 9.5 | 28 |
| 21 | Kymene | | 89 | — | — | — | — | 10.7 | — |
| 22 | None | | 9 | — | — | — | — | 9.4 | — |
| 23 | Pvam | | 23 | — | — | — | — | 7.0 | — |
| 24 | Kymene | | 19 | — | — | — | — | 8.8 | — |

Curing: heating 30 S @ 160 C. in a through air dryer

As shown above, retention of the softening agent in the samples drastically improved when a retention agent was added. For instance, when a retention agent was present, retention of the softening agent increased by at least 10% and, in some instances, by almost 300%. Samples made according to the present invention also had a relatively low slough, a relatively high wet tensile strength and a relatively high wet to dry tensile strength ratio.

Example 3

The effect of wet-end chemistry upon retention of WetSoft CTW silicone (containing amine functional groups) was tested.

Standard handsheets were constructed from untreated and pre-treated eucalyptus pulp. The untreated eucalyptus pulp was disintegrated for 1 minute in a British Pulp Disintegrator (BPD) at a specific pH. Then, Wetsoft CTW silicone, obtained from Wacker Chemical Corp., was added at 1.1% (wt) on dry pulp to the BPD contents. The disintegration was then completed (4 more minutes) and handsheets were made for silicone retention and physical testing. Wetsoft CTW pretreated pulp (SiPP-2) made at Aracruz, Brazil, was disintegrated in a similar manner and 2 Kg/T PAREZ as a retention agent was added to the BPD after 1 min at a given pH.

Sample 25 was made with eucalyptus pulp without any reactive silicon additive and no pH control.

Sample 26 was made with eucalyptus pulp and CTW was added in the BPD at a pH range of 3.5 to 4.

Sample 27 was made with eucalyptus pulp and CTW was added in the BPD at a pH of 7.5.

Sample 28 was made with Wetsoft CTW SiPP-2 pretreated pulp and did not contain any PAREZ retention agent.

Sample 29 was made with Wetsoft CTW SiPP-2 pretreated pulp and 2 kg/mt PAREZ retention agent was added at a pH of 4.

Sample 30 was made with Wetsoft CTW SiPP-2 pretreated pulp and 2 kg/mt PAREZ retention agent was added at a pH of 7.3.

The following results were obtained:

| Sample | CTW amount, % | CTW found, % | Retention, % | Tensile, N-m/g | Drop abs, sec |
|---|---|---|---|---|---|
| 25 | 0 | 0.0 | 0 | 12.21 | 0.79 |
| 26 | 1.10% | 0.5 | 45% | 2.56 | 0.95 |
| 27 | 1.10% | 0.23 | 21% | 4.48 | 1.03 |
| 28 | 0.71% | 0.44 | 62% | 2.08 | 0.95 |
| 29 | 0.71% | 0.53 | 75% | 5.56 | 2.56 |
| 30 | 0.71% | 0.39 | 54% | 7.19 | 2.35 |

As shown above, Sample 29 made according to the present invention significantly improved the wet retention of the functionalized polysiloxane. As shown by comparing Sample 29 to Sample 30, the retention of the polysiloxane was somewhat pH sensitive. Higher retention was achieved at a pH of 4 in comparison to a pH of greater than 7.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A fibrous product comprising:
    at least one fibrous web containing cellulosic fibers, at least a portion of the cellulosic fibers having been pretreated with a softening agent comprising a polysiloxane containing a plurality of first functional groups; the first functional groups contained on the polysiloxane comprise epoxy groups, an hydride groups, aldehyde groups, carboxylic groups, epihalohydrin groups, or mixtures thereof; and
    a retention agent contained in the fibrous web, the retention agent comprising a polymer containing a plurality of a second functional group, the second functional group comprising an amine group, an amide group, an anhydride group, an aldehyde group, an epoxy group, epihalohydrin group, or mixtures thereof, the retention agent being present in an amount sufficient to increase the retention of the polysiloxane on the cellulosic fibers under aqueous conditions as compared to a pretreated fibrous product without a retention agent;
    wherein the retention agent is reacted with the softening agent causing the softening agent to crosslink, the reaction facilitated by the addition of a catalyst.

2. A fibrous product as defined in claim 1, wherein the first functional groups contained on the polysiloxane comprise epoxy groups or anhydride groups and wherein the second functional groups contained on the retention agent comprise amine groups.

3. A fibrous product as defined in claim 1, wherein the first functional groups contained on the polysiloxane comprise epoxy groups, anhydride groups, or carboxylic groups, and wherein the retention agent comprises a glyoxylated polyacrylamide resin, a polyamide-polyamine-epichlorohydrin resin, a polyethyleneimine resin, a polyvinylamine resin, a copolymer of any of the above, or mixtures thereof.

4. A fibrous product as defined in claim 1, wherein the retention agent is present in an amount sufficient to increase the retention of the polysiloxane to the cellulosic fibers by at least 100% under aqueous conditions.

5. A fibrous product as defined in claim 1, wherein the retention agent is present in an amount sufficient to increase the retention of the polysiloxane to the cellulosic fibers by at least 200% under aqueous conditions.

6. A fibrous product as defined in claim 1, wherein the polysiloxane contains a plurality of third functional groups in addition to the first functional groups.

7. A fibrous product as defined in claim 6, wherein the third functional group is different than the first functional group and comprises a material selected from the group consisting of epoxy groups, an hydride groups, amine groups, aldehyde groups, carboxylic groups, epihalohydrin groups, vinyl groups, ether groups, imines groups, and amide groups.

8. A fibrous product as defined in claim 1, wherein the fibrous product comprises a facial tissue having a basis weight of from about 10 gsm to about 100 gsm.

9. A fibrous product as defined in claim 1, wherein the fibrous web has a wet-out time of less than about 200 seconds.

10. A fibrous product as defined in claim 1, wherein the fibrous web includes at least two fibrous layers, the pretreated cellulosic fibers being contained in at least one outer layer.

11. A fibrous product as defined in claim 1, wherein the retention agent was topically applied to the fibrous web while the fibrous web was wet.

12. A fibrous product as defined in claim 1, wherein the retention agent was combined with an aqueous suspension of the pretreated cellulosic fibers during formation of the fibrous web.

13. A fibrous product as defined in claim 1, wherein the fibrous web comprises a creped web.

14. A fibrous product as defined in claim 1, wherein the fibrous web comprises an uncreped, through-air dried web.

15. A fibrous product as defined in claim 1, wherein the fibrous product comprises a multi-ply product.

16. A diaper containing the fibrous web defined in claim 1, the diaper including an outer cover and an inner liner, the fibrous web being positioned in between the outer cover and the inner liner.

17. An adult incontinence product incorporating the fibrous web defined in claim 1.

18. A diaper as defined in claim 16, wherein the fibrous web is contained in an absorbent structure, the absorbent structure comprising superabsorbent particles.

19. A fibrous product as defined in claim 1, wherein the fibrous web comprises an airlaid web.

20. A fibrous product as defined in claim 1, wherein the cellulosic fibers comprise a blend of hardwood pulp fibers and softwood pulp fibers, wherein the ratio of hardwood pulp fibers to softwood pulp fibers is from about 9:1 to about 1:4.

21. A fibrous product as defined in claim 1, further comprising a skin conditioning agent comprising mineral oil, aloe extract, vitamin E, lotions, or mixtures thereof.

22. A fibrous product as defined in claim 1, wherein the retention agent is incorporated into the fibrous product in an amount from about 0.1 kg/T to about 20 kg/T.

23. A fibrous product as defined in claim 1, wherein the softening agent is incorporated into the fibrous product in an amount of about 1 kg/T to about 20 kg/T.

24. A fibrous product as defined in claim 1, wherein the fibrous product is a tissue product comprising multiple plies.

25. A fibrous product as defined in claim 24, wherein the softening agent is present only in the outer plies.

26. A fibrous product as defined in claim 1, wherein the pH during contact of the softening agent with the retention agent is less than about 5.

27. A fibrous product as defined in claim 1, wherein the reaction is further facilitated by subjecting the fibrous web to an energy source.

* * * * *